US012636463B2

(12) United States Patent
Min et al.

(10) Patent No.: US 12,636,463 B2
(45) Date of Patent: May 26, 2026

(54) APPARATUS FOR CONTROLLING BIOLOGICAL CLOCK AND SLEEP CYCLE THROUGH NON-INVASIVE BRAIN STIMULATION, CONTROL METHOD USING THE SAME, AND COMPUTER-READABLE STORAGE MEDIUM HAVING COMPUTER PROGRAM RECORDED THEREON FOR PROVIDING THE SAME

(71) Applicant: Korea University Research and Business Foundation, Seoul (KR)

(72) Inventors: Byoung-Kyong Min, Seoul (KR); SungYoung Park, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1094 days.

(21) Appl. No.: 17/707,193

(22) Filed: Mar. 29, 2022

(65) Prior Publication Data

US 2022/0323714 A1     Oct. 13, 2022

(30) Foreign Application Priority Data

Apr. 6, 2021    (KR) ........................ 10-2021-0044449

(51) Int. Cl.
*A61M 21/02* (2006.01)
*A61B 5/00* (2006.01)
(Continued)

(52) U.S. Cl.
CPC ......... *A61M 21/02* (2013.01); *A61N 1/36014* (2013.01); *A61M 2021/0038* (2013.01); *A61M 2021/0072* (2013.01)

(58) Field of Classification Search
CPC .......... A61M 21/02; A61M 2021/0038; A61M 2021/0072; A61M 21/00;
(Continued)

(56) References Cited

U.S. PATENT DOCUMENTS 9,821,162 B2    11/2017  Wu et al.
2015/0119689 A1 *  4/2015  Pascual-Leone ...... A61N 2/006
600/407
(Continued)

FOREIGN PATENT DOCUMENTS

KR         10-1833527 B1    2/2018
WO      WO 2018/109715 A1    6/2018

*Primary Examiner* — Carrie R Dorna
*Assistant Examiner* — Joshua Daryl D Lannu
(74) *Attorney, Agent, or Firm* — NSIP Law

(57) ABSTRACT

Provided are an apparatus, method, and computer-readable medium for controlling a biological clock and a sleep cycle. The apparatus may include a collection unit configured to receive a brain image of a subject, a stimulation control unit configured to analyze the brain image, set a target point to be stimulated in a target region located in the brain, and derive optimized stimulation conditions, and a stimulation unit configured to apply stimulation according to the stimulation conditions derived by the stimulation control unit, wherein the stimulation control unit comprises a target setting unit configured to analyze the brain image, acquire anatomical central coordinates of the target region, and set the target point according to the acquired central coordinates and a stimulation setting unit configured to configure a stimulation electrode combination according to the set target point and derive a stimulation function according to a stimulation modulation depth maximization function $(M_{MAX})$.

9 Claims, 11 Drawing Sheets

(51) Int. Cl.

| | |
|---|---|
| *A61B 5/01* | (2006.01) |
| *A61B 5/374* | (2021.01) |
| *A61M 21/00* | (2006.01) |
| *A61N 1/04* | (2006.01) |
| *A61N 1/36* | (2006.01) |
| *A61N 7/00* | (2006.01) |
| *A61N 7/02* | (2006.01) |
| *G16H 20/30* | (2018.01) |
| *G16H 30/40* | (2018.01) |
| *G16H 40/63* | (2018.01) |

(58) Field of Classification Search

CPC .. A61M 2205/3303; A61M 2205/3553; A61M 2205/502; A61M 2209/088; A61M 2210/0693; A61M 2230/10; A61M 2230/50; A61N 1/36014; A61N 1/36025; A61N 1/36031; A61N 1/0456; A61N 7/02; A61N 2007/0026; A61N 2007/0095; A61B 5/01; A61B 5/374; A61B 5/4812; A61B 5/4064; G16H 20/30; G16H 30/40; G16H 40/63

See application file for complete search history.

(56) References Cited

U.S. PATENT DOCUMENTS

| | | | |
|---|---|---|---|
| 2019/0021657 A1 | 1/2019 | Mohammadrezazadeh et al. | |
| 2019/0282812 A1 | 9/2019 | Simons et al. | |
| 2021/0370064 A1* | 12/2021 | Murphy | A61N 1/0484 |

* cited by examiner

Acquisition of central coordinates (x,y,z)

APPARATUS FOR CONTROLLING BIOLOGICAL CLOCK AND SLEEP CYCLE THROUGH NON-INVASIVE BRAIN STIMULATION, CONTROL METHOD USING THE SAME, AND COMPUTER-READABLE STORAGE MEDIUM HAVING COMPUTER PROGRAM RECORDED THEREON FOR PROVIDING THE SAME

CROSS-REFERENCE TO RELATED APPLICATION

This application claims priority to and the benefit of Korean Patent Application No. 10-2021-0044449, filed on Apr. 6, 2021, the disclosure of which is incorporated herein by reference in its entirety.

BACKGROUND

1. Field of the Invention

The present invention relates to an apparatus, method, and computer-readable medium for controlling a biological clock and a sleep cycle through non-invasive brain stimulation, and more particularly, to an apparatus, method, and computer-readable medium for controlling a biological clock and a sleep cycle through non-invasive brain stimulation by effectively stimulating a suprachiasmatic nucleus (SCN) region of the deep brain through non-invasive brain stimulation to regulate the sleep cycle as well as to control the biological clock.

2. Discussion of Related Art

The physiological activity of living things changes according to their own biological clock in the day and night cycle based on 24 to 25 hours, and various factors such as light, food, and temperature affect the biological clock.

At this time, a brain region that acts as a regulator, i.e., a pacemaker of the biological clock is the SCN located in the hypothalamus, which is the center of the brain, and the SCN controls the biological cycle of our entire body by sending a biological clock signal to each body part.

A problem with the biological clock is directly related to the sleep cycle, and the relationship between sleep duration or sleep quality and memory function is a very important issue and has been actively studied recently.

Also, recently, the relationship between the biological clock and carcinogenesis has come to the fore, and the relationship between the biological clock and various mental disorders such as insomnia, depression, and memory loss, which can cause dementia, has been consistently reported.

Various methods such as physical stimulation and invasive stimulation techniques as well as administration of drugs and hormones are used to treat biological-clock-related diseases.

Conventional treatment techniques for controlling the biological clock mainly rely on invasive stimulation techniques such as Deep Brain Stimulation (DBS), so there are risks associated with brain electrode implantation and management.

Also, in relation to biological clock regulation through deep brain stimulation, recently, there was a study report (Jones JR et al., Nat Neurosci. 2015, 18(3): 373-375) in which by utilizing optogenetic technology, it is possible to selectively express specific genes of neurons in the SCN region of mice to control the neural circuits of the SCN through light of a specific wavelength and to effectively reset (or synchronize) biological rhythms. The result of this study is based on a neurophysiological control method which is performed in an invasive manner after the skull of the brain is opened. Thus, there is a risk of infection and it is difficult for the general public to willingly undergo this unpleasant procedure.

In addition, since invasive gene expression technology called optogenetics is used to selectively stimulate brain cells in the SCN region of the deep brain, its effect has not been proven as a clinical technology applicable to the actual human body.

Also, no attempt has been reported to control the biological cycle using a non-invasive stimulation technique with proven clinical technical value and effectiveness.

Also, recently, in the case of non-invasive current stimulation, there is a research report that the deep brain can be stimulated by changing the frequency of alternating current sources to perform the stimulation (i.e., using a time variable and a phase difference) (Grossman N et al., Cell 2017, 169, 1029-1041). However, there are still technical limitations related to the effective enhancement of the stimulation effect of electric current stimulation to the deep brain.

As the related art, Korean Patent No. 10-1833527 (electrical stimulation device) has been disclosed.

SUMMARY OF THE INVENTION

In order to solve the above problems, the present invention is directed to providing an apparatus, method, and computer-readable medium for controlling a biological clock and a sleep cycle through non-invasive brain stimulation by effectively stimulating the SCN region of the deep brain through non-invasive brain stimulation to regulate the sleep cycle as well as to control the biological clock.

According to an aspect of the present invention, there is provided an apparatus for controlling a biological clock and a sleep cycle through non-invasive brain stimulation, the apparatus including a collection unit configured to receive a brain (MR) image of a subject, a stimulation control unit configured to analyze the brain image, set a target point to be stimulated in a target region located in the brain, and derive optimized stimulation conditions, and a stimulation unit configured to apply stimulation according to the stimulation conditions derived by the stimulation control unit, wherein the stimulation control unit includes a target setting unit configured to analyze the brain image, acquire anatomical central coordinates of the target region, and set the target point according to the acquired central coordinates, and a stimulation setting unit configured to configure a stimulation electrode combination according to the set target point and derive a stimulation function according to a stimulation modulation depth maximization function ($M_{MAX}$).

Here, the stimulation unit may be made of electric current or focused ultrasound. Also, the stimulation setting unit may include an electrode selection unit configured to configure the stimulation electrode combination according to the set target point and a stimulation optimization unit configured to set, as an objective function, a ratio between a stimulation depth value in the target region and a depth value of a brain region other than the target region and derive the stimulation function according to the $M_{MAX}$.

Also, the stimulation control unit may further include a biological rhythm setting unit configured to derive a biological rhythm loss function according to a difference between a target biological rhythm and a current biological rhythm according to initial biological rhythm information of the subject collected by the collection unit and configured to find a stimulation protocol function (S) optimized according to the stimulation conditions.

Also, the biological rhythm setting unit may include a loss function setting unit configured to set the target biological rhythm and the current biological rhythm on the basis of the initial biological rhythm information, calculate the difference between the target biological rhythm and the current biological rhythm, and set the calculated difference as the biological rhythm loss function, and a parameter optimization unit configured to optimize a stimulation parameter to determine the stimulation protocol function (S), and wherein when the biological rhythm loss function is greater than a set value, the stimulation unit applies stimulation according to the stimulation electrode combination, the stimulation function, and the stimulation protocol function.

Also, the stimulation control unit may further include a verification unit configured to, after the stimulation unit applies the stimulation, compare biological information before and after the stimulation and verify the optimized stimulation conditions.

According to another aspect of the present invention, there is provided a control method using an apparatus for controlling a biological clock and a sleep cycle through non-invasive brain stimulation, the control method including a target setting operation in which a stimulation control unit of the apparatus analyzes a brain image of a subject, acquires anatomical central coordinates of a target region, and sets a target point for stimulation according to the acquired central coordinates, a stimulation setting operation in which the stimulation control unit configures a stimulation electrode combination according to the set target point and derives a stimulation function, and a stimulation operation in which the stimulation unit of the apparatus applies stimulation according to the stimulation electrode combination and the stimulation function derived according to stimulation conditions.

Also, the control method may further include, after the stimulation setting operation, a biological rhythm setting operation in which the stimulation control unit derives a biological rhythm loss function according to a difference between a target biological rhythm and a current biological rhythm according to collected initial biological rhythm information of the subject and finds an optimized stimulation protocol function (S).

The biological rhythm setting operation may include a current value setting operation in which the stimulation control unit sets the current biological rhythm through the collected initial biological rhythm information of the subject, a target value setting operation in which the stimulation control unit sets the target biological rhythm, a loss function deriving operation in which the stimulation control unit calculates a difference between the target biological rhythm and the current biological rhythm and derives the biological rhythm loss function, and a parameter optimization operation in which the stimulation control unit optimizes a stimulation parameter and determines the stimulation protocol function (S), wherein in the stimulation operation, the stimulation unit determines whether to apply stimulation according to the biological rhythm loss function and uses the stimulation electrode combination, the stimulation function, and the stimulation protocol function (S) to apply stimulation.

According to another aspect of the present invention, there is provided a computer-readable recording medium having a computer program recorded thereon for providing the method of controlling a biological clock and a sleep cycle.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
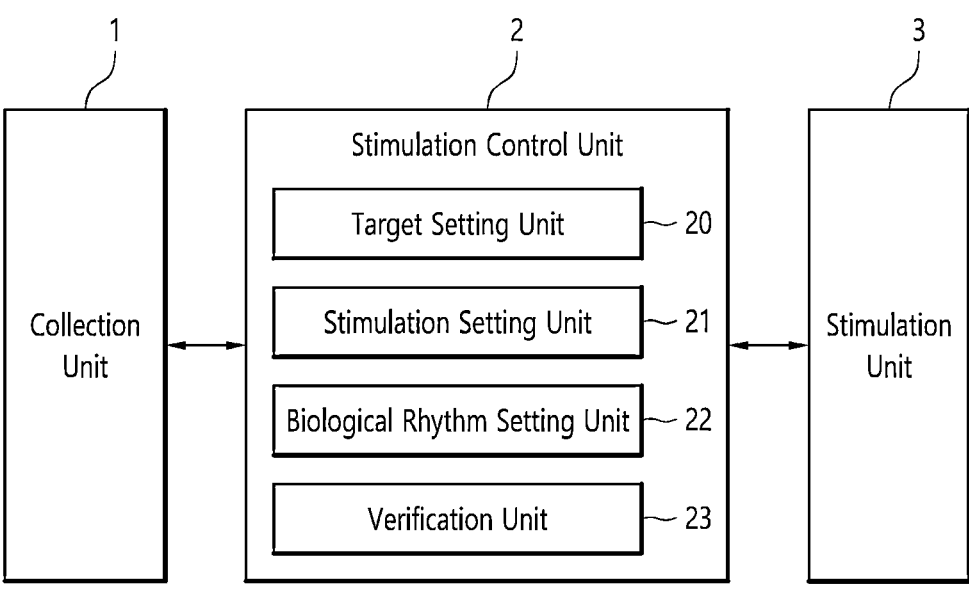
FIG. 1 is a block diagram showing a schematic configuration of an apparatus of controlling a biological clock and a sleep cycle through non-invasive brain stimulation according to an embodiment of the present invention.

Hereinafter, the description of the present invention with reference to the drawings is not limited to specific embodiments, and various modifications may be made and various embodiments may be provided. Also, it should be understood that the following description encompasses any modifications, equivalents and substitutes included in the spirit and scope of the present invention.

In the following description, terms such as first, second, etc. are terms used to describe various components, and their meanings are not limited thereto. The terms are used only for the purpose of distinguishing one component from other components.

Like reference numerals refer to like elements throughout the specification. As used herein, the singular forms "a," "an," and "one" are intended to include the plural forms as well, unless the context clearly indicates otherwise. It should be understood that the term "comprise," "include," or "have," when used herein, specify the presence of stated features, integers, steps, operations, elements, components, or combinations thereof but do not preclude the presence or addition of one or more other features, integers, steps, operations, elements, components, and/or combinations thereof.

Also, terms such as "-er," "-or," and "module" used herein refer to an element for performing at least one function or operation and may be implemented with hardware, software, or a combination thereof.

The present invention is directed to effectively delivering stimulation by setting a specific target for the SCN region and then providing optimal stimulation when stimulating the SCN, which is one deep brain region, through transcranial Current Stimulation (tCS) technology or focused ultrasound sonication (FUS) technology, which are non-invasive brain stimulation technologies.

In addition, the present invention is directed to regulating biological rhythms such as a sleep cycle and increasing the generation of sleep spindle brain waves during sleep, and thus it is possible to treat sleep disorders such as insomnia.

Hereinafter, an apparatus, method, and computer-readable medium for controlling a biological clock and a sleep cycle through non-invasive brain stimulation according to embodiments of the present invention will be described in detail with reference to the accompanying drawings.

Figure 2A:
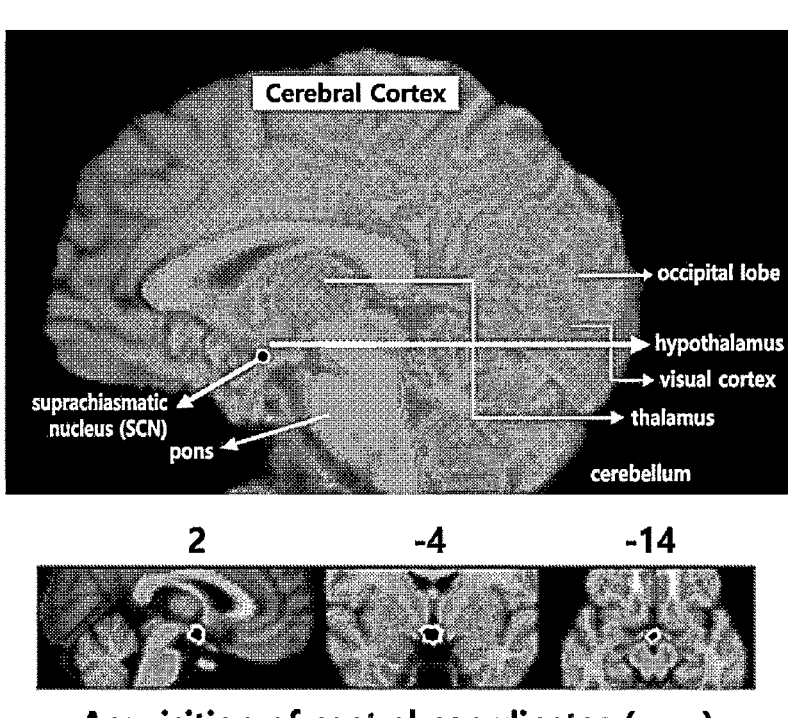
FIGS. 2A and 2B are exemplary diagrams showing central coordinates of the SCN obtained by analyzing a brain image and a target point that is set through the central coordinates by a target setting unit of FIG. 1.
Figure 2B:
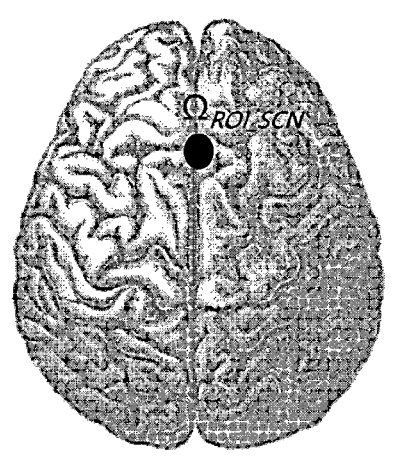
Figure 3:
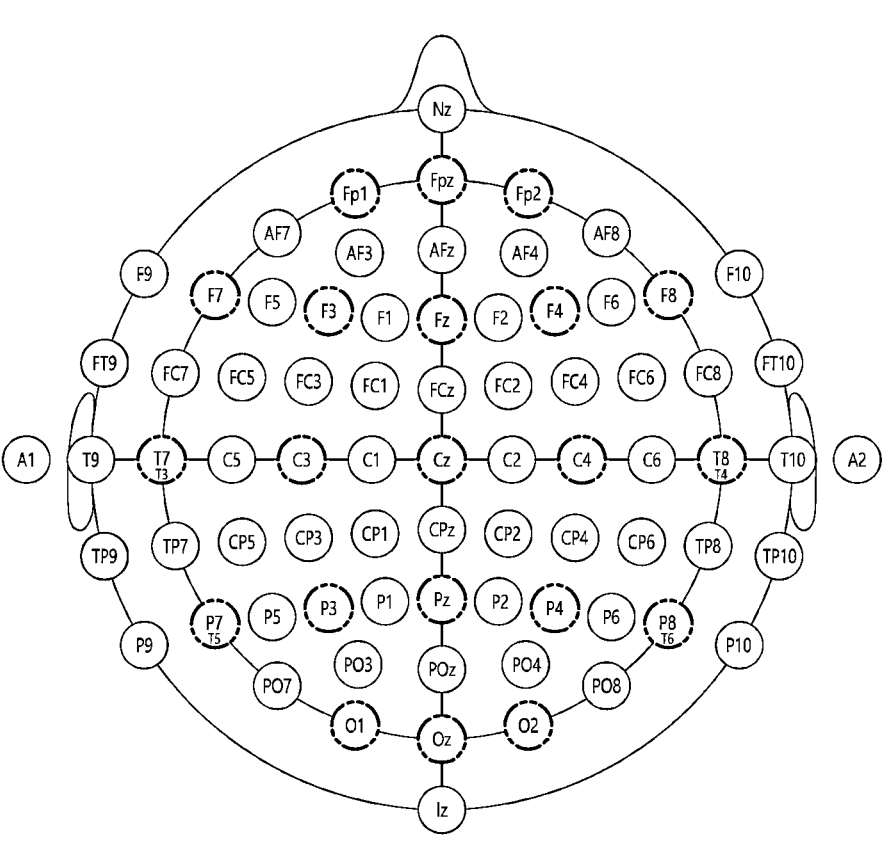
FIG. 3 is an exemplary view showing a scalp electrode position that can be stimulated by a stimulation unit made of a transcranial current stimulator of FIG. 1.
Figure 4:
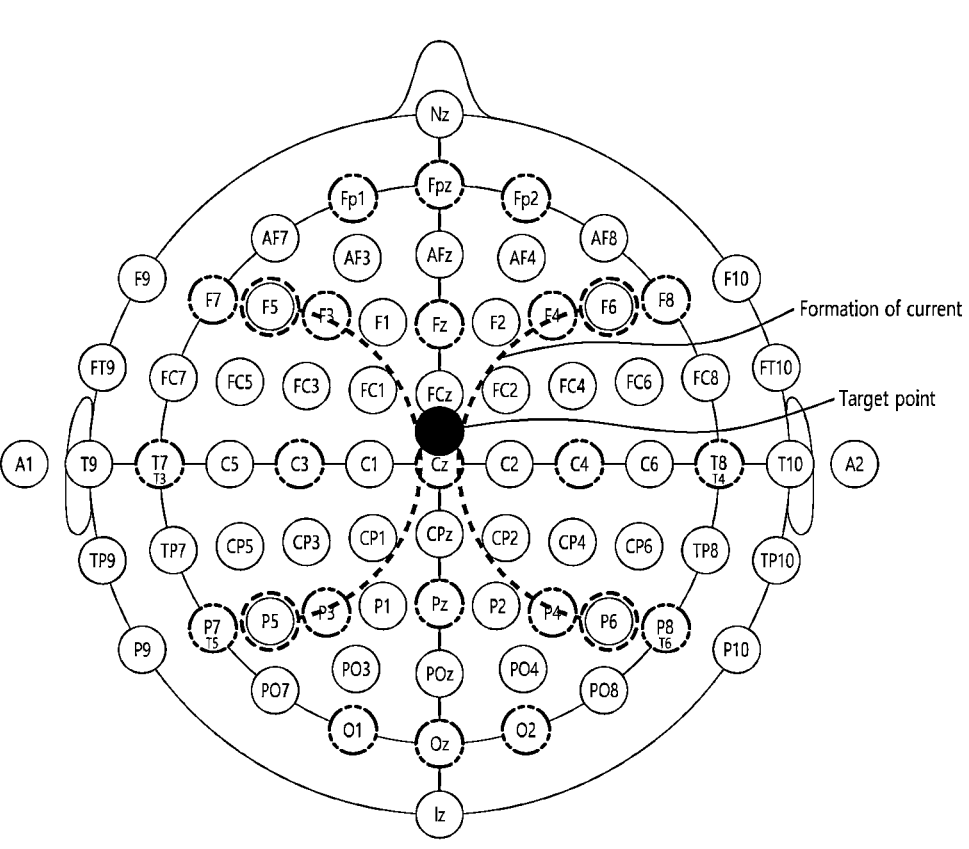
FIG. 4 is an exemplary diagram illustrating a stimulation electrode combination configured according to a target point in a stimulation setting unit of FIG. 1.
Figure 5:
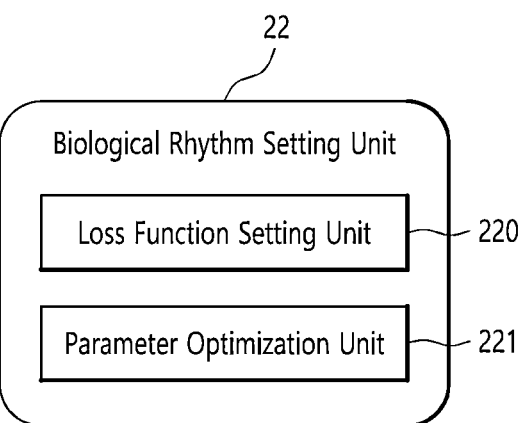
FIG. 5 is a block diagram showing a configuration of a biological rhythm setting unit of FIG. 1.
Figure 6:
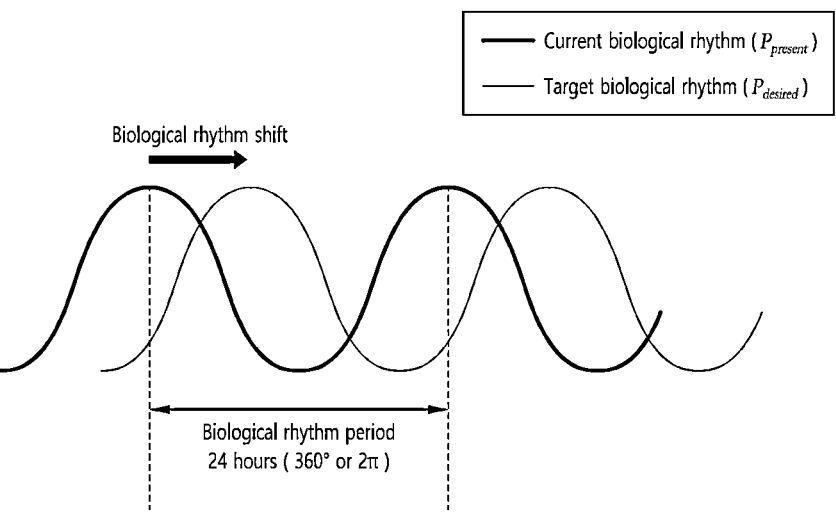
FIG. 6 is an exemplary diagram illustrating a current biological rhythm and a target biological rhythm set by a loss function setting unit of FIG. 5.
Figure 7:
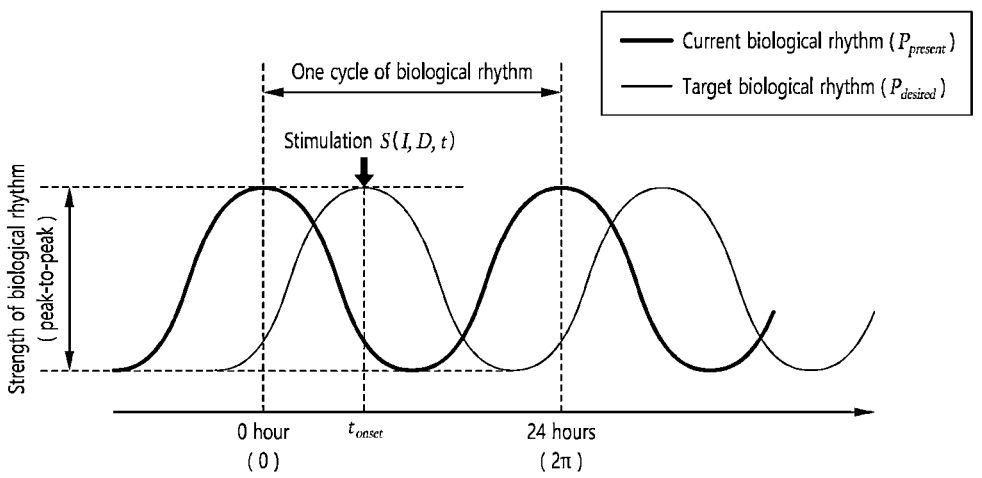
FIG. 7 is an exemplary diagram illustrating that stimulation is applied according to a stimulation protocol function by a stimulation unit of FIG. 1.

FIG. 1 is a block diagram showing a schematic configuration of an apparatus of controlling a biological clock and a sleep cycle through non-invasive brain stimulation according to an embodiment of the present invention. FIGS. 2A and 2B are exemplary diagrams showing central coordinates of the SCN obtained by analyzing a brain image and a target point that is set through the central coordinates by a target setting unit of FIG. 1. FIG. 3 is an exemplary view showing a scalp electrode position that can be stimulated by a stimulation unit made of a transcranial current stimulator of FIG. 1. FIG. 4 is an exemplary diagram illustrating a stimulation electrode combination configured according to a target point in a stimulation setting unit of FIG. 1. FIG. 5 is a block diagram showing a configuration of a biological rhythm setting unit of FIG. 1. FIG. 6 is an exemplary diagram illustrating a current biological rhythm and a target biological rhythm set by a loss function setting unit of FIG. 5. FIG. 7 is an exemplary diagram illustrating that stimulation is applied according to a stimulation protocol function by a stimulation unit of FIG. 1.

Referring to FIG. 1, the apparatus for controlling a biological clock and a sleep cycle through non-invasive brain stimulation according to an embodiment of the present invention (hereinafter referred to as a "biological clock and sleep cycle control apparatus") may receive a brain MR (magnetic resonance) image and initial biological rhythm information of a subject, optimize the conditions of stimulation based on the received brain image and initial biological rhythm information, and apply optimal stimulation to the subject.

To this end, the biological clock and sleep cycle control apparatus may include a collection unit 1, a stimulation control unit 2, and a stimulation unit 3. The collection unit 1 may receive and store a brain image of a subject. In this case, the brain image, which is a magnetic resonance image (MRI), may be received directly from an MRI apparatus or may be received from a terminal which is connected to an MRI apparatus or in which brain images are stored.

The stimulation control unit 2 may receive the brain image of the subject, set a target point to be stimulated in the SCN, and derive optimized stimulation conditions so that the stimulation unit 3 can apply the stimulation to the subject according to the derived stimulation conditions.

Here, the stimulation conditions may be a stimulation electrode combination corresponding to a position of electrodes applying stimulation, a stimulation function including information on the strength, frequency, and phase of stimulation, and the like.

Specifically, the stimulation control unit 2 may include a target setting unit 20 and a stimulation setting unit 21.

The target setting unit 20 may analyze the brain image of the subject and set the target point to be stimulated on the basis of a target region located in the brain. According to the present invention, stimulation is applied to the SCN region as a target. However, the present invention is not limited thereto and may be utilized in brain regions corresponding to various cognitive functions of the brain. Accordingly, the scope will be extended, and the corresponding region will be referred to as a target region.

More specifically, the target setting unit 20 may acquire the anatomical central coordinates (x, y, z) of the target region in the brain image as shown in FIG. 2A and may set a target point $\Omega_{ROI\_SCN}$ to be stimulated using the anatomical central coordinates as the center point as shown in FIG. 2B.

The stimulation setting unit 21 may configure the stimulation electrode combination according to the set target point and derive a stimulation function for stimulation.

To this end, the stimulation setting unit 21 may include an electrode selection unit and a stimulation optimization unit.

The electrode selection unit may configure the stimulation electrode combination according to the set target point. This is to derive an optimal electrode position on the basis of the set target point.

For example, the electrode selection unit may configure the stimulation electrode combination $_{N}C_{n}$ by selecting n electrodes according to target points from among a total of N electrodes of the stimulation unit 3. A more specific example will be described with reference to FIGS. 3 and 4.

When the stimulation unit 3 is composed of, for example, a 10-10 international system of EEG electrode placement such that electrodes are arranged as shown in FIG. 3, the electrode selection unit may configure a pair of F5 and P5 and a pair of F6 and P6 as stimulation electrode combinations such that the electrodes are symmetrical with respect to the target point and at least two electrodes are located on each side (See FIG. 4). Since this is only an example in the present invention, the present invention is not limited to the example in which the electrode pairs form a symmetric structure.

Also, the stimulation unit 3 may transmit information on the configured stimulation electrode combination to a terminal or may provide information on the configured stimulation electrode combination to the subject or a user by displaying the information through a display.

As described above, currents having different stimulation waveforms may be applied to electrodes located on both sides with respect to the target point as the center. This is because it is possible to expect stimulation enhancement by allowing electrodes at different positions to have different frequencies or phases and thus it is also possible to effectively stimulate the target region such as the SCN in the deep brain.

At this time, the stimulation function for the applied stimulation waveform may be derived by the stimulation optimization unit.

The stimulation optimization unit may derive the stimulation function according to a stimulation modulation depth maximization function $M_{MAX}$.

Here, two stimulation functions are required to apply currents having different stimulation waveforms to the stimulation electrode combination configured to form pairs on both sides, and the two stimulation functions A and B may be defined as in Equation 1 below.

$$A = a \sin \omega_A t \qquad \text{[Equation 1]}$$
$$B = b \sin \omega_B t$$

Here, a and b denote the size (amplitude) of waveforms, ωA and ωB denote phases, and t is time.

Meanwhile, a stimulation modulation depth function $M_{|\tilde{E}_{xyz}(t)|}$ is expressed by Equation 2 below.

$$M_{|\tilde{E}_{xyz}(t)|} = 2\min(|A \cdot u|, |B \cdot u|) \qquad \text{[Equation 2]}$$

Here, $\tilde{E}xyz(t)$ is the magnitude of current at the central coordinates (x, y, z) of the target region, and u is a unit vector having directionality in the whole three-dimensional brain structure.

Thus, the stimulation optimization unit may derive the stimulation function using the stimulation modulation depth maximization function $M_{MAX}$ defined by Equation 3 below. That is, the stimulation optimization unit is for deriving a stimulation function that maximizes the stimulation modulation depth so that the subject is stimulated under the optimized condition.

$$M_{MAX} = \max_u M_{|\tilde{E}_{xyz}(t)|} = 2\max_u \min(\|A\|\|\cos\alpha\|, \|B\|\|\cos(\alpha - \theta)\|) \qquad \text{[Equation 3]}$$

Here, considering the current waveforms corresponding to the stimulation functions A and B as vector types, θ is an angle (vector angle) representing the difference between A and B, and a is the difference between A and the projection plane of unit vector u. The maximum value is to be found under the condition of $\alpha \in [0, 2\pi]$.

At this time, since the stimulation depth value in the target region must be greater than the depth values of brain regions other than the target region, the stimulation optimization unit may set the ratio of the stimulation depth value ($M_{SCN}$) in the target region and the depth value $M_{non\_SCN}$ in the brain regions other than the target region as an objective function f(M) as in Equation 4 below.

$$f(M) = \left\| \frac{M_{SCN}}{M_{non\_SCN}} \right\| \qquad \text{[Equation 4]}$$

Here, $M_{SCN}$ is the stimulation depth value in the target region (e.g. SCN), and $M_{non\_SCN}$ is the depth value of the brain regions other than the target regions.

Thus, it is possible to derive the stimulation function according to the stimulation modulation depth maximization function $M_{MAX}$ under the condition in which the objective function f(M) is maximized Accordingly, the stimulation unit 3 may stimulate the subject using the stimulation electrode combination and stimulation function derived as described above.

Also, the stimulation control unit 2 may further include a biological rhythm setting unit 22 to regulate biological rhythms through stimulation.

The biological rhythm setting unit 22 may set an initial biological rhythm and a target biological rhythm through the collected initial biological rhythm information of the subject and may obtain a stimulation protocol function S under stimulation conditions in which stimulation is applied based on the initial biological rhythm and target biological rhythm. Accordingly, the stimulation unit 3 may be allowed to regulate the biological rhythm by applying stimulation according to the stimulation protocol function S. That is, it is possible not only to apply optimal stimulation to a set target but also to apply stimulation according to the cycle to regulate the biological rhythm.

Meanwhile, the collection unit 1 may collect the initial biological rhythm information of the subject so that the biological rhythm setting unit 22 can obtain the stimulation protocol function S.

In this case, the initial biological rhythm information may be information measured using one of an EEG signal measurement, a biosensor (core body temperature), a power spectrum frequency analysis, a Karolinska sleepiness scale, and a biological rhythm cycle value measured by a commercially available wearable device.

The EEG signal measurement may be made by measuring signals such as Fp1, Fp2; F3, Fz, F4; FC1, FC2; C3, Cz, C4; CP1, CP2; P3, Pz, P4; O1, Oz, and O2 such that regions such as the fronto-central, parietal, and occipital regions are included for each time-period through the electrode of the stimulation unit 3 formed as shown in FIG. 3.

Such information may be received through a terminal or may be received directly from a measurement device. However, the present invention is not limited thereto, and such information may be received through various methods.

Also, the initial biological rhythm information may include a sleep cycle $T_{sleep-wake}$ which is expressed with sleep and wake times.

Also, the initial biological rhythm information may include an individual's natural frequency (delta wave, theta wave, alpha wave, beta wave, gamma wave, etc.).

Also, the collection unit 1 may receive the subject's current biological rhythm information after the subject is stimulated by the stimulation unit 3.

Referring to FIG. 5, the biological rhythm setting unit 22 may include a loss function setting unit 220 and a parameter optimization unit 221.

The loss function setting unit 220 may set the current biological rhythm according to the collected initial biological rhythm information. That is, the biological rhythm of the initial biological rhythm information (phase information of the biological rhythm) may be set as the current biological rhythm.

Also, the loss function setting unit 220 may set a target biological rhythm. The loss function setting unit 220 sets the phase of the target biological rhythm.

Here, 24 hours, 360° or 2π(may be set as one cycle of the set biological rhythm, but the present invention is not limited thereto.

The loss function setting unit 220 may set, as a biological rhythm loss function, the difference between the phase value of the current biological rhythm and the phase value of the target biological rhythm set as shown in FIG. 6.

A biological rhythm loss function $L_{CR}$ which is set herein may be defined as in Equation 5 below.

$$L_{CR}(P) = \|P_{present} - P_{desired}\|_{P_{initial}} \qquad \text{[Equation 5]}$$

Here, $L_{CR}$ is the biological rhythm loss function, $P_{present}$ is the phase value of the current biological rhythm, $P_{desired}$ is the phase value of the target biological rhythm, and $P_{initial}$ is the phase value of the initial biological rhythm of the subject.

Also, after the subject is stimulated, the loss function setting unit 220 may re-calculate the biological rhythm loss function using the current biological rhythm information of the subject received by the collection unit 1.

The parameter optimization unit 221 may optimize a stimulation parameter to determine the stimulation protocol function S as shown in Equation 6 below. In this case, the optimization may include finding a value of the stimulation parameter that causes the stimulation protocol function S to have a maximum value.

$$S(I, D, t) = t_{duration} \times D_{fAM} \times \|I_{amplitude}\| \qquad \text{[Equation 6]}$$

Here, $t_{duration}$ is the stimulation time (time range), $f_{AM}$ is the frequency of the amplitude-modulated stimulation tuning waveform, $D_{fAM}$ is the power spectrum density of the stimulation tuning waveform, and $\|I_{amplitude}\|$ is the total stimulation size.

Also, the parameter optimization unit 221 may consider the natural frequency of the individual subject when optimizing the stimulation parameter and may set the frequency $f_{AM}$ of the stimulation tuning waveform as the natural frequency.

Also, the parameter optimization unit 221 may set the frequency ($f_{AM}$) of the stimulation tuning waveform by including a frequency band such as 4 to 6 Hz or 8 to 12 Hz (centered around 10 Hz), which is the action potential frequency of the SCN.

Accordingly, the stimulation unit 3 may determine whether to apply stimulation according to the biological rhythm loss function.

For example, when the biological rhythm loss function is greater than a set value, the stimulation unit 3 may apply stimulation according to the stimulation electrode combination, the stimulation function, and the stimulation protocol function S. Here, the set value may be "0" or a minimum value that can make the difference between the phase value of the target biological rhythm and the phase value of the current biological rhythm almost nonexistent.

As described above, by applying stimulation according to the stimulation protocol function S, the stimulation unit 3 may apply stimulation at an onset point $t_{onset}$ of the target biological rhythm as shown in FIG. 7.

Also, when the biological rhythm loss function re-calculated after the subject is stimulated is still larger than the set value, the parameter optimization unit 221 may optimize the stimulation parameter again, and then the stimulation unit 3 may stimulate the subject.

That is, the above process is repeated until the biological rhythm loss function is less than or equal to the set value.

After the stimulation unit 3 stimulates the subject, a verification unit 23 may compare biological information before and after the stimulation after the stimulation is applied and verify the optimized stimulation conditions (the stimulation electrode combination, the stimulation function, and the stimulation protocol function S).

Here, the biological information may include one or more of the brain image and the biological rhythm information.

However, the present invention is not limited thereto, and the biological information may include a variety of information.

As an example, the verification unit 23 may compare the brain images before and after the stimulation to determine whether the target region has been selectively stimulated. When it is determined that the selective stimulation is not preferably performed, the verification unit 23 may enable the target setting unit 20 and the stimulation setting unit 21 to resume operation so that the stimulation electrode combination and the stimulation function can be reset.

In an example, the verification unit 23 may receive the biological rhythm information before and after the stimulation using one of an EEG signal measurement, a biosensor (core body temperature), a power spectrum frequency analysis, a Karolinska sleepiness scale, and a biological rhythm cycle value measured by a commercially available wearable device, compare the received biological rhythm information before and after the stimulation, and check a change in biological rhythm data before and after the stimulation.

Here, when it is determined that the change in biological rhythm data is not desirable, the verification unit 23 may deliver a signal to the biological rhythm setting unit 22 to find the stimulation protocol function S again.

Thus, the verification unit 23 may verify whether the stimulation has been desirably performed, and when the stimulation is not desirably performed, the verification unit 23 may proceed again so that the optimal stimulation can be applied to the subject.

The stimulation unit 3, which is for stimulating the subject, may apply stimulation according to stimulation conditions (the stimulation electrode combination, the stimulation function, the stimulation protocol function, etc.) derived from the stimulation control unit 2. Also, the stimulation unit 3 may determine whether to apply stimulation according to the biological rhythm loss function.

Also, when the biological rhythm loss function re-calculated after the subject is stimulated is larger than the set value, the stimulation unit 3 may allow the stimulation control unit 2 to find the stimulation protocol function again.

The stimulation unit 3 may apply stimulation, for example, through electric current by applying the transcranial current stimulation technique.

When the transcranial current stimulation technique is applied as described above, the stimulation unit 3 is more preferably formed in a form to which the transcranial Alternating Current Stimulation (tACS) technique is applied, but the present invention is not limited thereto.

At this time, in the case of the transcranial current stimulation of the stimulation unit 3, a scalp electrode arrangement is based on a 10-20 or 10-10 system, but the present invention is not limited thereto. For a better understanding, a case in which the stimulation unit 3 is based on a 10-20 or 10-10 system has been described as an example, but the present invention is not limited thereto.

Also, in addition to the transcranial current stimulation technique, non-invasive focused ultrasound may be applied to the stimulation unit 3. The focused ultrasound may be effectively used for deep brain stimulation because it has excellent cranial penetration and spatially accurate target precision.

In this case, the stimulation unit 3 is configured as a high-density ultrasound transducer array instead of a high-density electrode used in the transcranial alternating current stimulation (tACS) technology. Thus, it is possible to focus the ultrasound on the target point of the deep brain, and it is also possible to optimize the stimulation on the SCN.

A control method using the apparatus for controlling the biological clock and the sleep cycle through non-invasive brain stimulation will be described in detail below.

Figure 8:
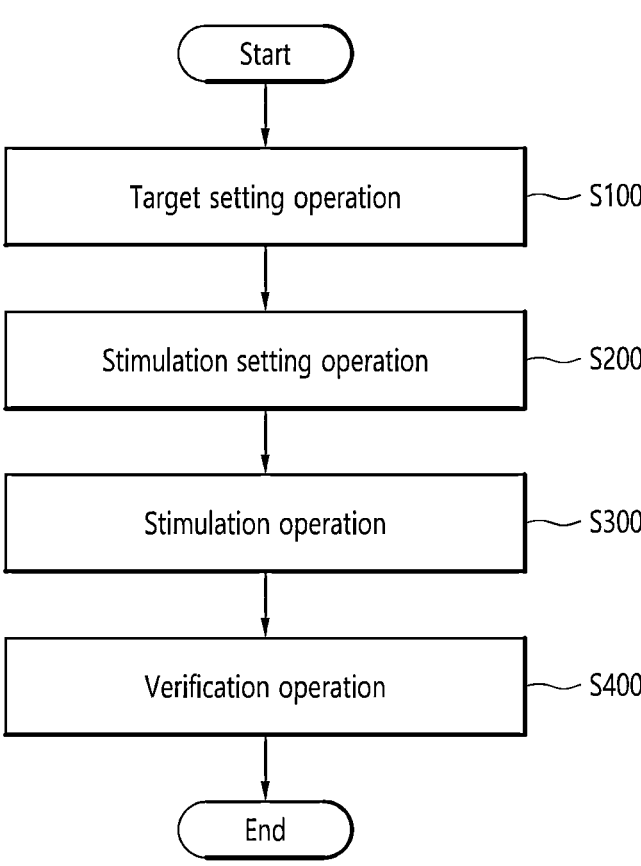
FIG. 8 is a flowchart illustrating a control method using the apparatus of controlling a biological clock and a sleep cycle through non-invasive brain stimulation according to an embodiment of the present invention.
Figure 9:
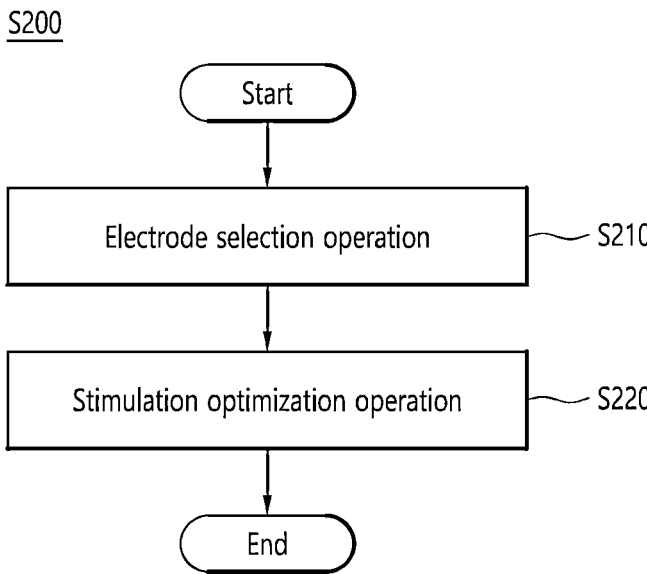
FIG. 9 is a flowchart sequentially illustrating operation S200 of FIG. 8.
Figure 10:
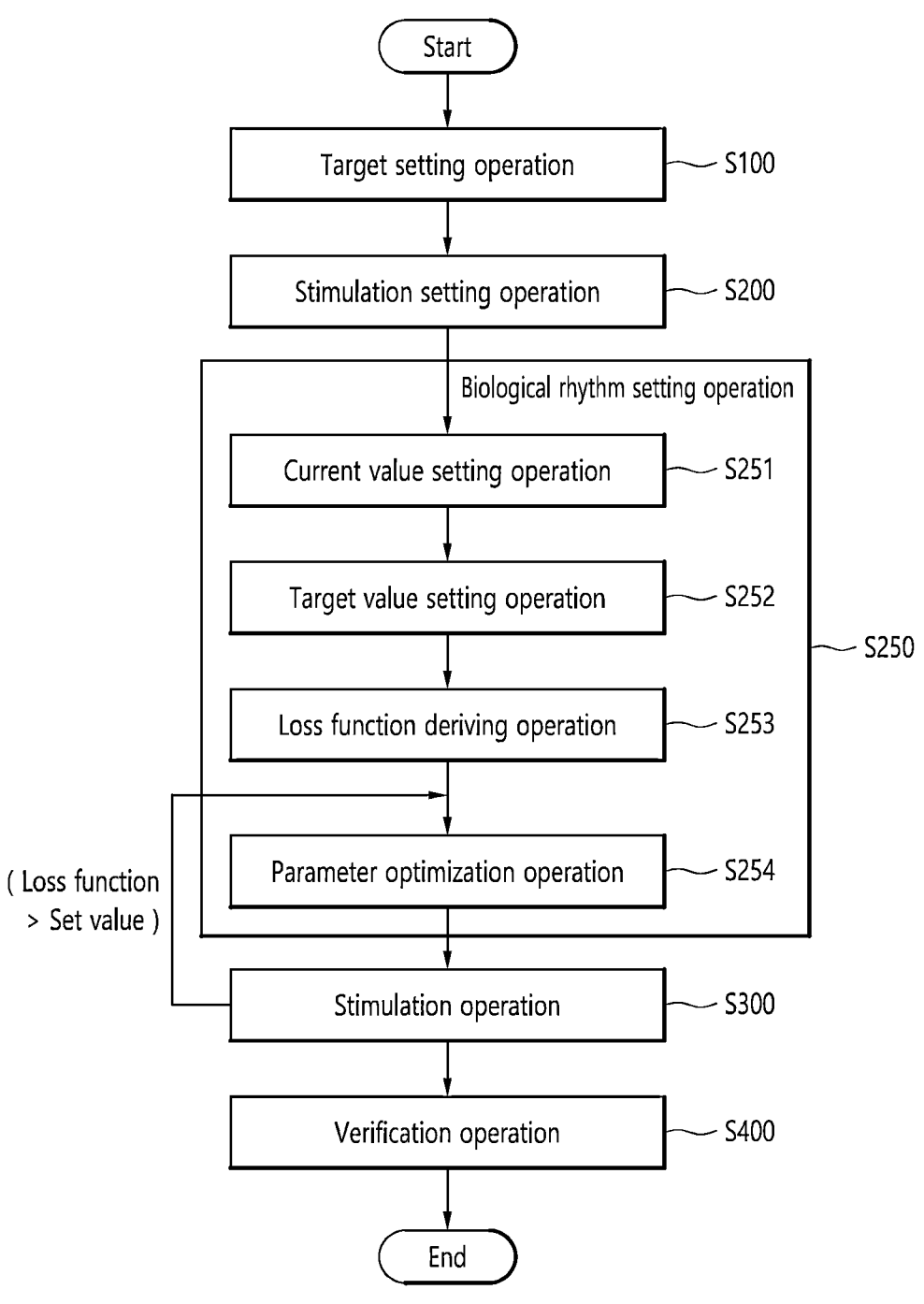
FIG. 10 is a flowchart illustrating an aspect in which the control method using the apparatus for controlling a biological clock and a sleep cycle through non-invasive brain stimulation according to an embodiment of the present invention further includes operation S250.

FIG. 8 is a flowchart illustrating a control method using the apparatus of controlling a biological clock and a sleep cycle through non-invasive brain stimulation according to an embodiment of the present invention. FIG. 9 is a flowchart sequentially illustrating operation S200 of FIG. 8. FIG. 10 is a flowchart illustrating an aspect in which the control method using the apparatus for controlling a biological clock and a sleep cycle through non-invasive brain stimulation according to an embodiment of the present invention further includes operation S250.

The control method using the apparatus for controlling a biological clock and a sleep cycle through non-invasive brain stimulation according to an embodiment of the present invention (hereinafter referred to as a "control method") may control the biological clock or regulate the biological rhythm.

The control method is basically a method for controlling the biological clock and may include receiving a brain image of a subject, setting a target point for stimulation according to the anatomical central coordinates of the SCN, and deriving a stimulation function according to the set target point to stimulate the set target point.

Referring to FIG. 8, the control method may include a target setting operation S100, a stimulation setting operation S200, a stimulation operation S300, and a verification operation S400. The detailed description was given when the apparatus was described above, and thus a detailed description thereof will be omitted.

In the target setting operation S100, the stimulation control unit 2 of the biological clock and sleep cycle control apparatus may analyze a brain image of a subject, acquire the brain anatomical central coordinates of a target region, and set a target point for stimulation according to the acquired central coordinates.

In the stimulation setting operation S200, the stimulation control unit 2 may configure a stimulation electrode combination according to the set target point and derive a stimulation function.

Referring to FIG. 9, operation S200 may include an electrode selection operation S210 and a stimulation optimization operation S220.

The electrode selection operation S210 may include configuring a stimulation electrode combination according to the set target point. In this case, the stimulation electrode combination may be configured around the target point.

The stimulation optimization operation S220 may include setting, as an objective function, the ratio between the stimulation depth value in the target region and the depth value of the brain region other than the target region and derive a stimulation function according to the stimulation modulation depth maximization function ($M_{MAX}$).

In this case, two stimulation functions may be derived so that currents having different stimulation waveforms are applied to one side and the other side with respect to the target point.

In the stimulation operation S300, the stimulation unit 3 may stimulate the subject according to the stimulation function and the stimulation electrode combination derived according to the stimulation conditions.

After operation S300, the verification operation S400 may include comparing biological information before and after the stimulation to the subject and verifying conditions for the stimulation (the stimulation electrode combination and the stimulation function).

Meanwhile, referring to FIG. 10, the control method using the apparatus for controlling a biological clock and a sleep cycle through non-invasive brain stimulation according to an embodiment of the present invention may further include a biological rhythm setting operation S250.

The biological rhythm setting operation S250 is an operation of setting factors for regulating the biological rhythm to reset (or synchronize) the sleep cycle and the like. In the biological rhythm setting operation S250, the collection unit 1 may collect initial biological rhythm information of the subject, and the stimulation control unit 2 may derive a biological rhythm loss function according to the difference between a target biological rhythm and the current biological rhythm corresponding to the initial biological rhythm information and derive an optimized stimulation protocol function S.

To this end, the biological rhythm setting operation S250 may include a current value setting operation S251, a target value setting operation S252, a loss function deriving operation S253, and a parameter optimization operation S254.

The detailed description was given when the apparatus was described above, and thus a detailed description thereof will be omitted.

In the current value setting operation S251, the collection unit 1 of the biological clock and sleep cycle control apparatus may collect initial biological rhythm information of a subject, and the stimulation control unit 2 may set a current biological rhythm using the collected initial biological rhythm information.

In the target value setting operation S252, the stimulation control unit 2 may set a target biological rhythm.

The loss function deriving operation S253 may include deriving a biological rhythm loss function by calculating the difference between the current biological rhythm and the target biological rhythm.

The parameter optimization operation S254 may include optimizing a stimulation parameter to determine a stimulation protocol function S.

Thus, in the stimulation operation S300, the stimulation unit 3 may determine whether to apply stimulation according to the biological rhythm loss function. When it is determined to apply stimulation, the stimulation unit 3 may stimulate the subject using the stimulation electrode combination, the stimulation function, and the stimulation protocol function S.

That is, in operation S300, when the biological rhythm loss function is greater than a set value, the stimulation unit 3 may stimulate the subject according to the stimulation electrode combination, the stimulation function, and the stimulation protocol function S. On other hand, when the biological rhythm loss function is less than or equal to the set value, the stimulation unit 3 may stop the stimulation.

Also, in operation S300, when applying stimulation, the collection unit 1 may receive the current biological rhythm information of the subject after the stimulation, and the stimulation control unit 2 may be allowed to re-calculate the biological rhythm loss function.

Thus, in operation S300, the stimulation unit 3 may compare the setting value and the re-calculated biological rhythm loss function and may repeat operations S250 to S254 when it is determined that the biological rhythm loss function is still greater than the set value. On the other hand, the process may end when it is determined that the re-calculated biological rhythm loss function is less than or equal to the set value in operation S300.

In addition, the present invention can be implemented by storing computer-readable code in a computer-readable storage medium. The computer-readable storage medium includes any type of storage apparatus in which data readable by a computer system is stored.

The computer-readable code is configured to perform operations implementing the method when the stimulation conditions are optimized by the biological clock and sleep cycle control apparatus while a brain image or initial biological rhythm information of a subject is input to the computer-readable storage medium. The computer-readable code may be implemented in various programming languages. Also, functional programs, code, and code segments for implementing the present invention can be readily programmed by those skilled in the art.

Examples of the computer-readable storage medium include a read-only memory (ROM), a random-access memory (RAM), CD-ROMs, magnetic tapes, floppy disks, optical data storage devices, etc., and include implementation in the form of a carrier wave (e.g., transmission over the Internet). The computer-readable storage medium may be distributed over network-coupled computer systems so that the computer-readable code can be stored and executed in a distributed fashion.

As described above, with the apparatus, method, and computer-readable medium for controlling a biological clock and a sleep cycle through non-invasive brain stimulation according to embodiments of the present invention, by effectively stimulating the SCN region of the deep brain through non-invasive brain stimulation, it is possible to control the biological clock and regulate the sleep cycle.

More specifically, by applying stimulation after setting a target point for the SCN to be stimulated based on an individual brain imaging MRI, it is possible to locally stimulate the SCN region to effectively control the neuronal function of the SCN region.

In addition, it is possible to regulate biological rhythms (a sleep cycle, etc.) by applying stimulation according to the target biological rhythm, and it is also possible to expect a therapeutic effect on sleep disorders such as insomnia by applying stimulation in the form of cross-frequency tuning.

With the apparatus, method, and computer-readable medium for controlling a biological clock and a sleep cycle through non-invasive brain stimulation according to embodiments of the present invention, it is possible to control the biological clock and regulate the sleep cycle by effectively stimulating the SCN region of the deep brain through non-invasive brain stimulation.

More specifically, by applying stimulation after setting anatomical coordinate values for each individual subject at a target point for the SCN to be stimulated based on the corresponding individual subject's brain imaging MRI, it is possible to locally stimulate the SCN region to effectively control the neuronal function of the SCN region.

In addition, it is possible to regulate biological rhythms (a sleep cycle, etc.) by applying stimulation according to the target biological rhythm, and it is also possible to expect a therapeutic effect on sleep disorders such as insomnia by applying stimulation in the form of cross-frequency coupling.

Although the embodiments of the present invention have been described with reference to the accompanying drawings, those skilled in the art will understand that the present invention may be embodied in other specific forms without departing from the technical spirit or essential features of the present invention. Therefore, the embodiments described above are illustrative in all respects and not restrictive.

What is claimed is:

1. An apparatus for controlling a biological clock and a sleep cycle through non-invasive brain stimulation, the apparatus comprising:

a collection unit implemented using hardware, software, or a combination thereof and including a processor-based control circuit, configured to receive a brain MR (magnetic resonance) image of a subject;

a stimulation control unit implemented using hardware, software, or a combination thereof and including a processor-based control circuit, configured to analyze the brain image, set a target point to be stimulated in a target region located in the brain, and derive optimized stimulation conditions; and a stimulation unit including at least one electrode or at least one ultrasound transducer, configured to apply stimulation according to the stimulation conditions derived by the stimulation control unit, wherein the stimulation control unit comprises:

a target setting unit implemented using hardware, software, or a combination thereof and including a processor-based control circuit, configured to analyze the brain image, acquire anatomical central coordinates of the target region, and set the target point according to the acquired central coordinates; and a stimulation setting unit implemented using hardware, software, or a combination thereof and including a processor-based control circuit, configured to configure a stimulation electrode combination for the stimulation unit according to the set target point and derive a stimulation function according to a stimulation modulation depth maximization function ($M_{MAX}$) defined as maximizing a ratio of stimulation depth in the target region to stimulation depth outside the target region.

2. The apparatus of claim 1, wherein the stimulation setting unit comprises:

an electrode selection unit implemented using hardware, software, or a combination thereof and including a processor-based control circuit, configured to configure the stimulation electrode combination according to the set target point; and a stimulation optimization unit implemented using hardware, software, or a combination thereof and including a processor-based control circuit, configured to set, as an objective function, a ratio between a stimulation depth value in the target region and a depth value of a brain region other than the target region and derive the stimulation function according to the stimulation modulation depth maximization function ($M_{MAX}$).

3. The apparatus of claim 1, wherein the stimulation control unit further comprises a biological rhythm setting unit comprising at least one processor, configured to derive a biological rhythm loss function according to a difference between a target biological rhythm and a current biological rhythm according to initial biological rhythm information of the subject collected by the collection unit and configured to find a stimulation protocol function(S) optimized according to the stimulation conditions.

4. The apparatus of claim 3, wherein the biological rhythm setting unit comprises:

a loss function setting unit comprising at least one processor, configured to set the target biological rhythm and the current biological rhythm on the basis of the initial biological rhythm information, calculate the difference between the target biological rhythm and the current biological rhythm, and set the calculated difference as the biological rhythm loss function; and a parameter optimization unit comprising at least one processor, configured to optimize a stimulation parameter to determine the stimulation protocol function(S), and wherein when the biological rhythm loss function is greater than a set value, the stimulation unit applies stimulation according to the stimulation electrode combination, the stimulation function, and the stimulation protocol function.

5. The apparatus of claim 1, wherein the stimulation control unit further comprises a verification unit comprising at least one processor, configured to, after the stimulation unit applies the stimulation, compare biological information before and after the stimulation and verify the optimized stimulation conditions.

6. A control method using an apparatus for controlling a biological clock and a sleep cycle through non-invasive brain stimulation, the control method comprising:

a target setting operation in which a stimulation control unit of the apparatus analyzes a brain image of a subject, acquires anatomical central coordinates of a target region, and sets a target point for stimulation according to the acquired central coordinates;

a stimulation setting operation in which the stimulation control unit configures a stimulation electrode combination according to the set target point and derives a stimulation function according to a stimulation modulation depth maximization function (Mmax); and a stimulation operation in which the apparatus's stimulation unit applies stimulation according to the stimulation electrode combination and the stimulation function derived according to stimulation conditions.

7. The control method of claim 6, further comprising, after the stimulation setting operation, a biological rhythm setting operation in which the stimulation control unit derives a biological rhythm loss function according to a difference between a target biological rhythm and a current biological rhythm according to collected initial biological rhythm information of the subject and finds an optimized stimulation protocol function(S).

8. The control method of claim 7, wherein the biological rhythm setting operation comprises:

a current value setting operation in which the stimulation control unit sets the current biological rhythm through the collected initial biological rhythm information of the subject;

a target value setting operation in which the stimulation control unit sets the target biological rhythm;

a loss function deriving operation in which the stimulation control unit calculates the difference between the target biological rhythm and the current biological rhythm and derives the biological rhythm loss function; and a parameter optimization operation in which the stimulation control unit optimizes a stimulation parameter and determines the stimulation protocol function(S), and wherein in the stimulation operation, the stimulation unit determines whether to apply stimulation according to the biological rhythm loss function and uses the stimulation electrode combination, the stimulation function, and the stimulation protocol function(S) to apply stimulation.

9. A non-transitory computer-readable recording medium having a computer program recorded thereon for providing the control method of claim 6.

* * * * *